United States Patent
Boutoussov

(10) Patent No.: US 7,957,440 B2
(45) Date of Patent: Jun. 7, 2011

(54) DUAL PULSE-WIDTH MEDICAL LASER

(75) Inventor: Dmitri Boutoussov, Dana Point, CA (US)

(73) Assignee: Biolase Technology, Inc., Irvine, CA (US)

( * ) Notice: Subject to any disclaimer, the term of this patent is extended or adjusted under 35 U.S.C. 154(b) by 0 days.

(21) Appl. No.: 12/028,817

(22) Filed: Feb. 10, 2008

(65) Prior Publication Data

US 2008/0212624 A1 Sep. 4, 2008

Related U.S. Application Data

(62) Division of application No. 11/191,594, filed on Jul. 27, 2005, now Pat. No. 7,630,420.

(51) Int. Cl.
*H01S 3/00* (2006.01)
*A61B 18/18* (2006.01)

(52) U.S. Cl. ........... 372/38.02; 372/25; 372/30; 372/31; 372/70; 606/10; 606/11

(58) Field of Classification Search .......... 372/25, 372/30, 31, 38.02, 70; 606/10, 11
See application file for complete search history.

(56) References Cited

U.S. PATENT DOCUMENTS

| | | | |
|---|---|---|---|
| 3,051,906 A * | 8/1962 | Haynes | 327/105 |
| 3,679,863 A | 7/1972 | Houldcroft et al. | |
| 3,679,998 A | 7/1972 | Dahlinger | |
| 3,914,648 A | 10/1975 | Friedman et al. | |
| 3,991,296 A | 11/1976 | Kojima et al. | |
| 4,005,333 A | 1/1977 | Nichols | |
| 4,087,705 A * | 5/1978 | Barnes | 327/177 |
| 4,092,864 A | 6/1978 | Romanowski | |
| 4,276,518 A | 6/1981 | Ferguson | |
| 4,550,275 A | 10/1985 | O'Loughlin | |
| 4,724,299 A | 2/1988 | Hammeke | |
| 4,770,811 A | 9/1988 | Myers | |
| 4,826,431 A | 5/1989 | Fujimura et al. | |
| 4,862,888 A | 9/1989 | Yessik | 606/4 |
| 4,908,030 A | 3/1990 | Linkow et al. | |
| 4,910,438 A | 3/1990 | Farnsworth | |
| 4,913,142 A | 4/1990 | Kittrell et al. | |
| 4,931,047 A | 6/1990 | Broadwin et al. | |
| 4,985,027 A | 1/1991 | Dressel | |
| 5,086,378 A | 2/1992 | Prince | |

(Continued)

FOREIGN PATENT DOCUMENTS

DE 3840126 A1 5/1990

(Continued)

OTHER PUBLICATIONS

U.S. Appl. No. 60/591,933, filed Jul. 27, 2004, Rizoiu, Ioana M.

(Continued)

*Primary Examiner* — Jessica T Stultz
*Assistant Examiner* — Joshua King
(74) *Attorney, Agent, or Firm* — Stout, Uxa, Buyan & Mullins, LLP

(57) ABSTRACT

A laser device that includes a dual pulse-width laser-pumping circuit generates long and short laser pulses. The laser-pumping circuit employs a single power supply with dual high voltage outputs that are selectable under control of a user. The laser device conveniently generates long and short laser pulses or a mix of the two for performing specialized surgical procedures.

7 Claims, 3 Drawing Sheets

U.S. PATENT DOCUMENTS

| | | | |
|---|---|---|---|
| 5,092,773 A | 3/1992 | Levy | |
| 5,102,410 A | 4/1992 | Dressel | |
| 5,151,029 A | 9/1992 | Levy | |
| 5,199,870 A | 4/1993 | Steiner et al. | |
| 5,221,561 A | 6/1993 | Flicstein et al. | 427/534 |
| 5,237,331 A | 8/1993 | Henderson et al. | |
| 5,242,454 A | 9/1993 | Gundlach et al. | |
| 5,263,950 A | 11/1993 | L'Esperance, Jr. | |
| 5,267,856 A | 12/1993 | Wolbarsht et al. | |
| 5,313,481 A | 5/1994 | Cook et al. | |
| 5,318,562 A | 6/1994 | Levy et al. | |
| 5,334,019 A | 8/1994 | Goldsmith et al. | |
| 5,374,266 A | 12/1994 | Kataoka et al. | |
| 5,388,988 A | 2/1995 | Groisser et al. | |
| 5,401,171 A | 3/1995 | Paghdiwala | |
| 5,409,376 A | 4/1995 | Murphy | |
| 5,498,935 A * | 3/1996 | McMahan et al. | 315/241 P |
| 5,552,675 A | 9/1996 | Lemelson | |
| 5,554,172 A | 9/1996 | Horner et al. | |
| 5,570,182 A | 10/1996 | Nathel et al. | |
| 5,574,247 A | 11/1996 | Nishitani et al. | |
| 5,611,797 A | 3/1997 | George | |
| 5,694,046 A | 12/1997 | Hillerich et al. | |
| 5,723,864 A | 3/1998 | Atkinson et al. | |
| 5,729,562 A | 3/1998 | Birx et al. | |
| 5,741,247 A * | 4/1998 | Rizoiu et al. | 606/10 |
| 5,755,751 A | 5/1998 | Eckhouse | |
| 5,764,672 A | 6/1998 | Ukita et al. | |
| 5,785,521 A | 7/1998 | Rizoiu et al. | |
| 5,820,627 A | 10/1998 | Rosen et al. | |
| 5,825,958 A | 10/1998 | Gollihar et al. | |
| 5,828,803 A | 10/1998 | Eckhouse | 385/88 |
| 5,869,805 A | 2/1999 | Beyer et al. | |
| 5,968,037 A | 10/1999 | Rizoiu et al. | |
| 6,080,148 A | 6/2000 | Damasco et al. | 606/10 |
| 6,083,218 A | 7/2000 | Chou | |
| 6,086,367 A | 7/2000 | Levy | |
| 6,106,516 A | 8/2000 | Massengill | |
| 6,118,521 A | 9/2000 | Jung et al. | |
| 6,193,711 B1 | 2/2001 | Connors et al. | 606/12 |
| 6,223,987 B1 | 5/2001 | Knowles et al. | |
| 6,231,567 B1 | 5/2001 | Rizoiu et al. | |
| 6,254,597 B1 | 7/2001 | Rizoiu et al. | |
| 6,288,499 B1 | 9/2001 | Rizoiu et al. | 315/200 A |
| 6,315,772 B1 | 11/2001 | Marchitto et al. | |
| 6,350,123 B1 | 2/2002 | Rizoiu et al. | |
| 6,389,193 B1 | 5/2002 | Kimmel et al. | |
| 6,449,301 B1 | 9/2002 | Wu et al. | |
| 6,512,782 B1 | 1/2003 | Hsia et al. | 372/25 |
| 6,544,256 B1 | 4/2003 | Rizoiu et al. | |
| 6,561,803 B1 | 5/2003 | Rizoiu et al. | |
| 6,567,582 B1 | 5/2003 | Rizoiu et al. | |
| 6,610,053 B1 | 8/2003 | Rizoiu et al. | |
| 6,616,447 B1 | 9/2003 | Rizoiu et al. | |
| 6,616,451 B1 | 9/2003 | Rizolu et al. | |
| 6,669,685 B1 | 12/2003 | Rizoiu et al. | |
| 6,701,181 B2 | 3/2004 | Tang et al. | |
| 6,744,790 B1 | 6/2004 | Tilleman et al. | |
| 6,821,272 B2 | 11/2004 | Rizoiu et al. | |
| 6,878,899 B2 | 4/2005 | Smart | |
| 6,902,290 B2 | 6/2005 | Watts et al. | |
| 7,097,639 B1 | 8/2006 | Almeida | 606/9 |
| 2002/0149324 A1 * | 10/2002 | Rizoiu et al. | 315/200 A |
| 2003/0069567 A1 | 4/2003 | Eckhouse et al. | 606/9 |
| 2003/0100824 A1 | 5/2003 | Warren et al. | |
| 2003/0227953 A1 * | 12/2003 | Hsia et al. | 372/53 |
| 2005/0137655 A1 | 6/2005 | MacFarland | |
| 2005/0143792 A1 | 6/2005 | Jay | |
| 2006/0020309 A1 | 1/2006 | Altshuler et al. | |

FOREIGN PATENT DOCUMENTS

| | | |
|---|---|---|
| DE | 4138468 | 3/1993 |
| EP | 0181199 | 5/1986 |
| EP | 0192833 | 9/1986 |
| EP | 0454312 A2 | 10/1991 |
| EP | 0454312 A3 | 10/1991 |
| GB | 2 023 330 | 12/1979 |
| GB | 2297610 A | 8/1996 |
| JP | 5945092 | 3/1984 |
| JP | 5200045 A | 9/1993 |
| JP | 5506601 A | 9/1993 |
| JP | 11511386 A | 10/1999 |
| JP | 200301465 | 1/2003 |
| JP | 2003070722 A | 3/2003 |
| WO | 9004358 A1 | 5/1990 |
| WO | 96 41657 | 12/1996 |
| WO | WO 97 07928 A3 | 3/1997 |
| WO | WO 9707928 | 3/1997 |
| WO | WO 97 45165 | 4/1997 |

OTHER PUBLICATIONS

U.S. Appl. No. 60/601,415, filed Aug. 13, 2004, Rizoiu, Ioana M.
U.S. Appl. No. 60/610,757, filed Sep. 18, 2004, Rizoiu, Ioana M.
U.S. Appl. No. 11/042,824, filed Jan. 24, 2005, Boutoussov, Dmitri.
U.S. Appl. No. 11/192,334, filed Jul. 27, 2005, Boutoussov, Dmitri.
International Search Report & Written Opinion, Sep. 2, 2005, PCT/US05/00849.
International Search Report & Written Opinion, Jul. 31, 2006, PCT/US06/00989.
International Search Report & Written Opinion, Oct. 25, 2006, PCT/US05/28891.
International Search Report, Dec. 10, 1998, PCT/US98/12357.
Written Opinion, Apr. 15, 1999, PCT/US98/12357.
European Search Report, Jun. 6, 2005, EP 05 07 5231.
Partial European Search Report, Apr. 6, 2000, EP 98 92 9060.
T.S. Fahlen, Efficient Quarter-Joule KrF Laser with Corona Preionization, IEEE Journal of Quantum Electronics, vol. QE-15, No. 5, pp. 311-312. May 5, 1979.
Bernard Grob, Basic Electronics, Glencoe division of Macmillan/McGraw-Hill, pp. 690-681. 1989.
New Laser—Matter Interaction Concept to Enhance Tissue Cutting Efficiency by Ioana M. Rizoiu and Larry G. DeShazer, published in SPIE col. 2134A Laser-Tissue Interaction V(1994)/309.
International Search Report, Jun. 30, 2008, PCT/US08/051963.
International Search Report, May 23, 2008, PCT/US08/051967.
Rizoiu, Ioana and Levy, Guy C. "Efficiency of Bone Ablation with an Nd:YAG Laser Beam Delivered with a Cooling Spray" SPIE vol. 1882 Laser-Tissue Interaction IV (1993), pp. 316-321.
Rizoiu, Ioana and Levy, Guy C. "Morphological Changes of Dentin and Enamel after Ablation with an Experimental Laser System" SPIE vol. 2128, pp. 282-288.
Supplementary European Search Report, EP 05711358 (PCT/US2005/000852), mailed Feb. 8, 2010.

* cited by examiner

DUAL PULSE-WIDTH MEDICAL LASER

CROSS-REFERENCE TO RELATED APPLICATIONS

This application is a divisional of U.S. application Ser. No. 11/191,594, filed Jul. 27, 2005, now U.S. Pat. No. 7,630,420 the entire contents of which are incorporated herein by reference.

BACKGROUND OF THE INVENTION

1. Field of the Invention

The present invention relates generally to electromagnetic energy emitting devices and, more particularly, to pulsed medical treatment laser devices.

2. Description of Related Art

A variety of electromagnetic laser energy generating architectures have existed in the prior art. A solid-state laser system, for example, generally comprises a laser rod for emitting coherent light and a source for stimulating the laser rod to emit the coherent light. Flashlamps are typically used as stimulation sources for middle infrared lasers between 2.5 microns ($\mu m$) and 3.5 $\mu m$, such as Er, Cr:YSGG and Er:YAG laser systems. The flashlamp is driven by a flashlamp current, which comprises a predetermined pulse shape and a predetermined frequency.

The flashlamp current drives the flashlamp at the predetermined frequency, to thereby produce an output flashlamp light distribution having substantially the same frequency as the flashlamp current. This output flashlamp light distribution from the flashlamp drives the laser rod to produce coherent light at substantially the same predetermined frequency as the flashlamp current.

Medical applications, such as those requiring the excision of soft human tissue, may in some instances require or benefit from two opposite tissue effects. The first effect may relate to laser cutting of tissue with controlled hemostasis, minimal to no bleeding, and attenuated or eliminated charring of cut surfaces. The second effect may relate to laser cutting with bleeding in order, for example, to stimulate post-operative healing when tissue is brought together. The second effect can be particularly important or relevant, for example, in grafting applications.

Prior art methods of generating these first and second effects can include employing distinctly different devices for each type of tissue cutting. Some prior art methods of performing first and second effect procedures may include employing systems capable of generating different wavelengths of laser energy. For example, wavelengths of about 1 $\mu m$ and about 3 $\mu m$ may be generated using $CO_2$ and Erbium type lasers, respectively. Overhead time and effort that may be required in switching between two medical devices can be disadvantages of this approach. Extra time and attendant discomfort from a point of view of a patient undergoing such procedures may represent additional disadvantages.

A need exists in the prior art for laser devices capable of rapidly and efficiently transitioning between varying characteristics or modes of operation, to facilitate, for example, different desired cutting effects or procedures such as for facilitating both hemostatic-type and bleeding-type tissue cutting effects

SUMMARY OF THE INVENTION

An exemplary implementation of the method present invention addresses these needs by providing first and second high voltage outputs from a single power supply. A laser-pumping source (e.g., a flashlamp) also can be provided, the laser-pumping source being capable of exciting a laser that may be used for cutting tissue. The first and second high voltage outputs drive respective first and second pulse-forming networks capable of generating respective first and second pulse outputs that pump the laser-pumping source according to the exemplary implementation of the method. Pulses produced by the first pulse-forming network may be relatively short, and pulses produced by the second pulse-forming network may be relatively long.

An embodiment of the present invention comprises a laser device having a single power supply capable of supplying a first high voltage output at a first voltage level and a second high voltage output at a second voltage level. The embodiment further comprises a laser-pumping source and first and second pulse-forming networks. The respective first and second pulse-forming networks are capable of receiving respective first and second high voltage outputs and are further capable of driving the laser-pumping source.

While the apparatus and method has or will be described for the sake of grammatical fluidity with functional explanations, it is to be expressly understood that the claims, unless expressly formulated under 35 U.S.C. 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. 112 are to be accorded full statutory equivalents under 35 U.S.C. 112.

Any feature or combination of features described herein are included within the scope of the present invention provided that the features included in any such combination are not mutually inconsistent as will be apparent from the context, this specification, and the knowledge of one skilled in the art. For purposes of summarizing the present invention, certain aspects, advantages and novel features of the present invention are described herein. Of course, it is to be understood that not necessarily all such aspects, advantages or features will be embodied in any particular embodiment of the present invention. Additional advantages and aspects of the present invention are apparent in the following detailed description and claims that follow.

DETAILED DESCRIPTION OF THE INVENTION

Figure 1:
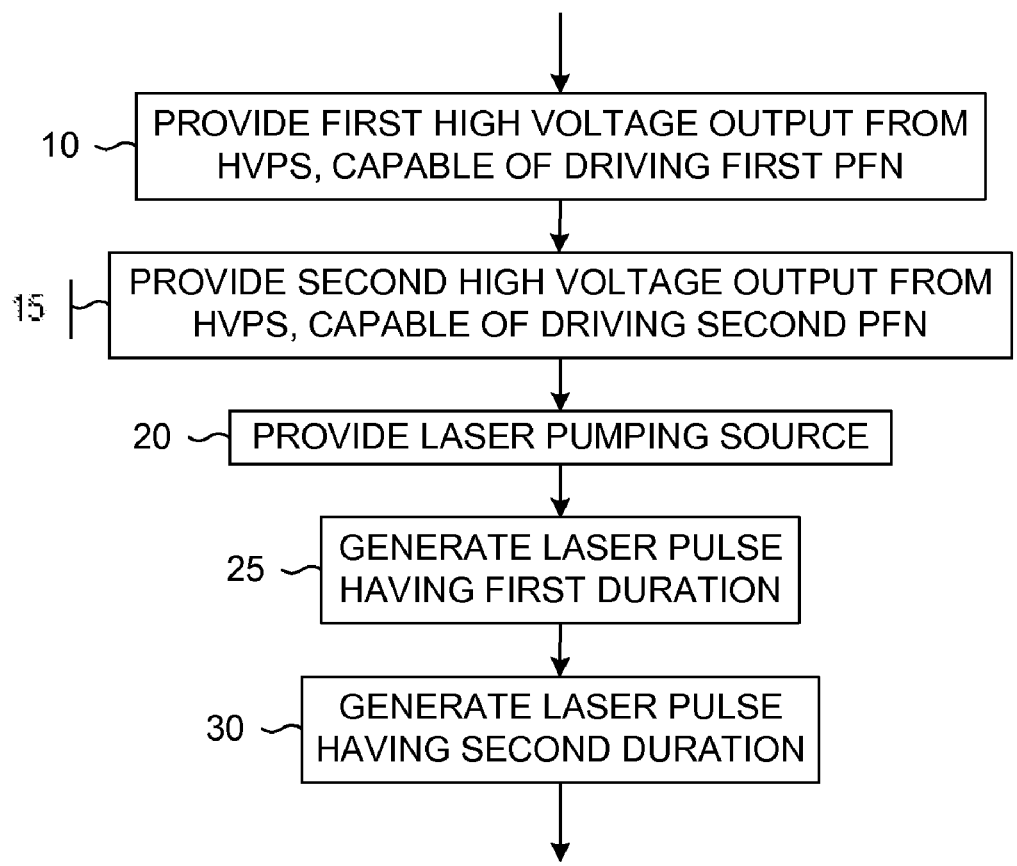
FIG. 1 is a flow diagram describing an implementation of the method of the present invention.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims. It is to be understood and appreciated that the process steps and structures described herein do not cover a complete architecture and process flow for operation of laser devices. The present invention may be practiced in conjunction with various structures and techniques that are conventionally used in the art, and only so much of the commonly practiced items are included herein as are necessary to provide an understanding of the present invention. The present invention has applicability in the field of electromagnetic treatment devices in general. For illustrative purposes, however, the following description pertains to a medical laser device and a method of operating the medical laser device to perform tissue treatments and surgical functions.

Referring more particularly to the drawings, FIG. 1 is a flow diagram describing an implementation of the method of the present invention. This implementation of the method provides a first high voltage output from a high voltage power supply (HVPS) at step 10. The first high voltage output is capable of driving a first pulse-forming network (PFN). A second high voltage output from the HVPS is provided at step 15. The second high voltage output is capable of driving a second pulse-forming network. An exemplary embodiment of the high voltage outputs described herein can provide about 1500 volts from the first high voltage output and about 500 volts from the second high voltage output. A laser-pumping source is further provided at step 20 according to the implementation. In a representative embodiment, the laser-pumping source can comprise a flashlamp capable of stimulating emission of coherent light by a laser device such as, for example, an Er:YSGG or Er, Cr:YSGG solid state laser. At step 25 of the implementation, a laser pulse having a first duration is generated by pumping the laser-pumping source with the first pulse-forming network output. Similarly, at step 30 a laser pulse having a second duration may be generated by pumping the laser-pumping source with the second pulse-forming network output.

Figure 2:
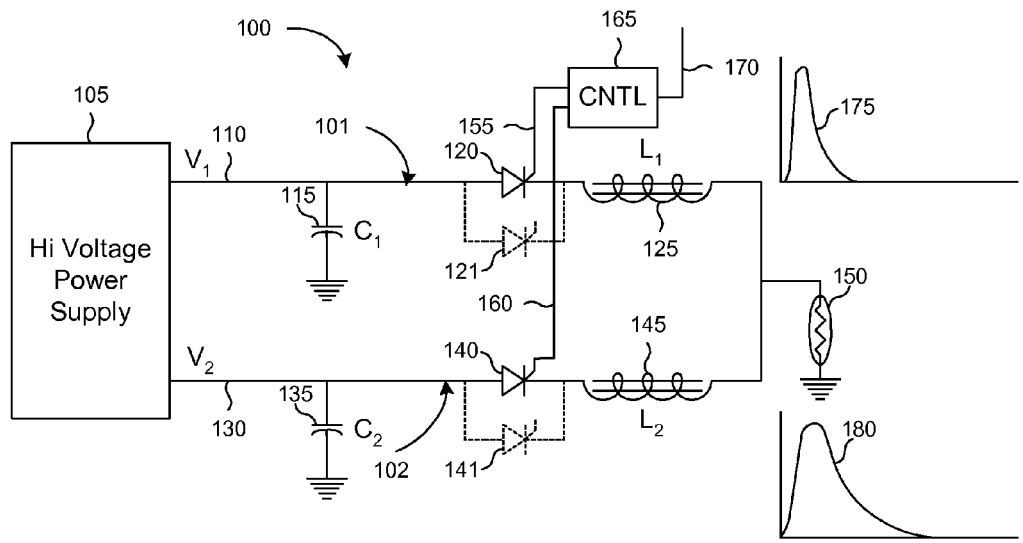
FIG. 2 is a schematic diagram illustrating an embodiment of a dual pulse-width flashlamp driving circuit.

An example of a circuit capable of driving a flashlamp from first and second high voltage outputs is described below with reference to FIG. 2. A relatively detailed implementation of the circuit of FIG. 2 is disclosed in FIGS. 2$p$ and 3$p$ of the above-referenced U.S. Provisional Application No. 60/591,933, filed Jul. 27, 2004 and entitled DUAL PULSE-WIDTH MEDICAL LASER. An Er:YSGG or Er, Cr:YSGG solid state laser, which is capable of generating electromagnetic energy having a wavelength in a range of about 2.70 microns (µm) to 2.80 µm, typically 2.78 µm, may be driven with the architecture of this circuit. Parameters of the first and second pulse-forming networks may be adjusted to produce, respectively, pulses having relatively short and long durations. In a typical embodiment, relatively short pulses having durations of, for example, about 140 microseconds (µs) are produced by the first pulse-forming network, and relatively long pulses having durations of, for example, about 400 µs are produced by the second pulse-forming network. Repetition rates for the pulses may range, for example, from about 1 to 50 pulses/second.

A partial schematic diagram of an embodiment of a dual pulse-width analog flashlamp driving circuit 100 according to the present invention is shown in FIG. 2, comprising a high voltage power supply 105 capable of producing dual, i.e., respective first and second, high voltage outputs 110 and 130 using methods known to those skilled in the art. In the illustrated embodiment, the first and second high voltage outputs 110 and 130 are provided on different nodes so that they may be generated at different times or have different values. The illustrated embodiment of the dual pulse-width analog flashlamp driving circuit 100 further comprises a first pulse-forming network 101 and a second pulse-forming network 102 connected to respective first and second high voltage outputs 110 and 130. First and second pulse-forming networks 101 and 102 are further connected to a flashlamp 150 that may function as a pumping source for a laser (not shown).

The first pulse-forming network 101 in the illustrated embodiment comprises a first capacitor 115, a first switching transistor 120, (for example, an insulated gate bipolar transistor (IGBT)), and a first inductor 125. The first capacitor 115 is connected between the first high voltage output 110 and ground. The first high voltage output 110 further is connected to the first inductor 125 through the first switching transistor 120, and the flashlamp 150 is electrically connected between the first inductor 125 and ground. The first pulse-forming network 101 and the second pulse-forming network 102 may be similar in form to a circuit such as that shown in FIG. 3 of the above-referenced U.S. application Ser. No. 11/033,032 filed Jan. 10, 2005 and entitled ELECTROMAGNETIC ENERGY DISTRIBUTIONS FOR ELECTROMAGNETICALLY INDUCED MECHANICAL CUTTING. The second pulse-forming network 102, which is similar in form to the first pulse-forming network 101, comprises a second capacitor 135, a second switching transistor 140, and a second inductor 145. The second high voltage output 130 is applied to a terminal of the second capacitor 135, which has another terminal connected to ground. The second high voltage output 130 also is coupled through a second switching transistor 140 to the second inductor 145, which is connected to the flashlamp 150.

In typical embodiments of the dual pulse-width analog flashlamp driving circuit 100, first and second capacitors 115 and 135 may assume values of, respectively, about 30 microfarads (µF) to about 70 µF, with an exemplary value being about 50 µF, and about 300 µF to about 600 µF, with an exemplary value being about 400 µF. First and second capacitors may receive respective first and second high voltage outputs 110 and 130. The first high voltage output 110 in an illustrative embodiment has a value ranging from about 1200 volts to about 1500 volts at an impedance level capable of charging the first capacitor 115 at a rate of about 1500 Joules per second (J/s). The second high voltage output 130 in the embodiment may range from about 200 volts to about 500 volts at an impedance level capable of charging the second capacitor 135 at a rate of about 1 J/s. The first inductor 125 may comprise an inductance of about 30 microhenries (µH) to about 70 µH, such as a solid core inductor having a rated inductance of about 50 µH in an exemplary embodiment. The second inductor 145 may comprise an inductance of about 800 µH to about 1200 µH, such as a solid core inductor having an inductance of about 1 millihenry (mH). The flashlamp 150 may comprise a 450 to 900 torr source, such as a 700 torr source. Control signals 155 and 160 from a control device 165 may be applied to terminals of transistors 120 and 140 in order to enable operation of the first pulse-forming network 101 or the second pulse-forming network 102. Enabling the first pulse-forming network 101 may generate relatively short laser pulses, and enabling the second pulse-forming network 102 may generate relatively long laser pulses according to a typical mode of operation of the illustrated embodiment. A user input 170, which may comprise, for example, a switch on a laser handset (not shown), may specify parameters (e.g., user adjustable parameters) such as pulse duration and/or pulse repetition rate. In some embodiments, additional switching transistors 121 and 141, shown in phantom in FIG. 2, may be provided in order to increase current capacity of the first and second pulse-forming networks 101 and 102.

A relatively short current pulse 175 may be produced by the first pulse-forming network 101 in the embodiment of the dual pulse-width analog flashlamp driving circuit 100 illustrated in FIG. 2. The second pulse-forming network 102 may produce a relatively long current pulse 180 with parameters chosen substantially as described herein.

Figure 3:
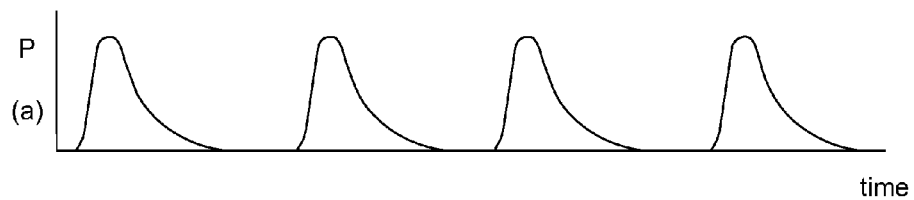
FIG. 3 is a plot depicting short, long, and mixed laser pulses generated by the dual pulse-width flashlamp driving circuit shown in FIG. 2.
Figure 3:
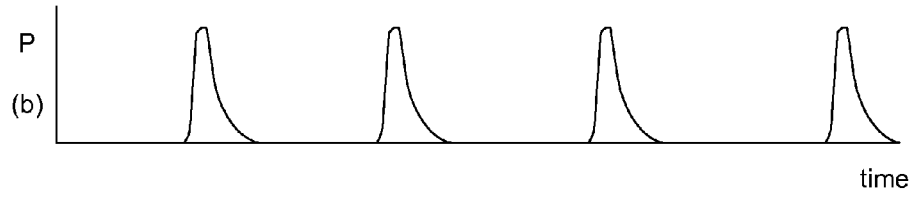
Figure 3:
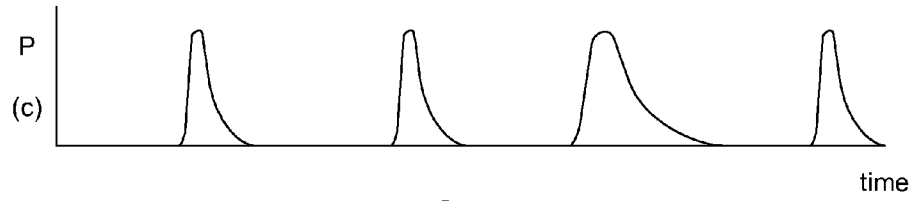

FIG. 3 is a chart illustrating three exemplary chains (a, b, c) of laser pulses capable of being produced by a laser device driven by the dual pulse-width analog flashlamp driving circuit embodiment 100 shown in FIG. 2. Chain (a) illustrates laser energy generated according to relatively long pulses. Chain (b) illustrates relatively short pulses of laser energy, and chain (c) depicts a mixture of relatively long and short pulses. A user may select a type of pulse chain to be produced using, for example, a user input 170 (FIG. 2).

Long pulses generated by the embodiment illustrated in FIG. 2 may be used to achieve an objective of cutting tissue with good hemostasis, no bleeding, and no charring of a cut surface. Conversely, short pulses generated by the same embodiment may provide for cutting with bleeding in order to promote post-operative healing. In another application, short pulses may be employed in the cutting of hard tissue (e.g., tooth enamel, dentin, bone) while long pulses may be used in cutting soft tissue (e.g., periodontal, mucosa, liver, kidney) and to perform thermal modifications. Examples of long pulse and short pulse applications are described in, for example, U.S. application Ser. No. 11/033,032, filed Jan. 10, 2005 and entitled ELECTROMAGNETIC ENERGY DISTRIBUTION FOR ELECTROMAGNETICALLY INDUCED MECHANICAL CUTTING and U.S. Provisional Application No. 60/601,415, filed Aug. 13, 2004 and entitled DUAL PULSE-WIDTH MEDICAL LASER WITH PRESETS. Indication, for instance, pulses of greater power for hard tissue application. According to certain implementations of the present invention, use of the methods and apparatus described herein are not restricted to medical (or dental) applications alone, and similar methods and apparatus contemplated by the present invention may be applied in industrial applications, such as for removing and shaping semiconductor materials.

Figure 4:
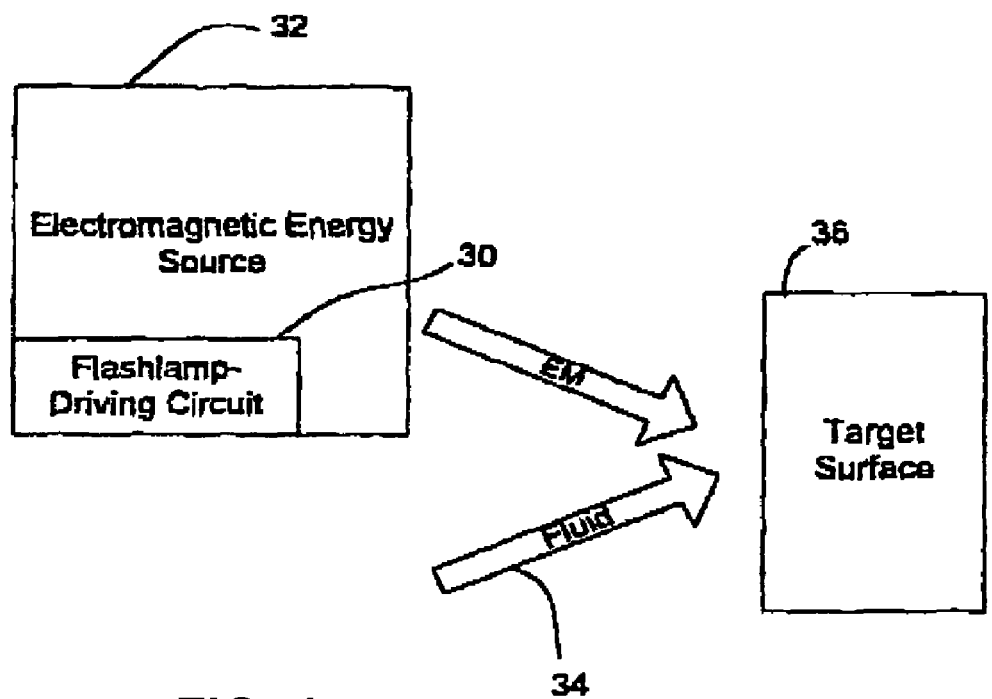
FIG. 4 is a block diagram showing a fluid output used in combination with an electromagnetic energy source having a flashlamp driving circuit in accordance with the present invention.

Corresponding or related structure and methods described in the following patents assigned to BioLase Technology, Inc., are incorporated herein by reference in their entireties, wherein such incorporation includes corresponding or related structure (and modifications thereof) in the following patents which may be (i) operable with, (ii) modified by one skilled in the art to be operable with, and/or (iii) implemented/used with or in combination with any part(s) of, the present invention according to this disclosure, that/those of the patents, and the knowledge and judgment of one skilled in the art: U.S. Pat. No. 5,741,247; U.S. Pat. No. 5,785,521; U.S. Pat. No. 5,968,037; U.S. Pat. No. 6,086,367; U.S. Pat. No. 6,231,567; U.S. Pat. No. 6,254,597; U.S. Pat. No. 6,288,499; U.S. Pat. No. 6,350,123; U.S. Pat. No. 6,389,193; U.S. Pat. No. 6,544,256; U.S. Pat. No. 6,561,803; U.S. Pat. No. 6,567,582; U.S. Pat. No. 6,610,053; U.S. Pat. No. 6,616,447; U.S. Pat. No. 6,616,451; U.S. Pat. No. 6,669,685; U.S. Pat. No. 6,744,790 and U.S. Pat. No. 6,821,272. For example, output optical energy distributions 60 from the flashlamp 150 of the illustrated embodiment of the present invention may be useful for optimizing or maximizing a cutting effect of an electromagnetic energy source 32, such as a laser that is driven by the flashlamp 150. The laser output can be directed, for example, into fluid (e.g., an atomized distribution of fluid particles) 34 above a target surface 36, as shown in FIG. 4. An apparatus for directing electromagnetic energy into an atomized distribution of fluid particles above a target surface is disclosed in the above-referenced U.S. Pat. No. 5,741,247. As disclosed at column 4, lines 31 and 43 and FIG. 3, this document discloses pulse durations (i.e., pulse widths) having different durations (i.e., a first pulse shorter than a second pulse). The long and/or short pulses can impart large amounts of energy into the fluid (e.g., atomized fluid particles) which preferably comprises water, to thereby expand the fluid (e.g., fluid particles) and apply disruptive (e.g., mechanical) cutting forces to the target surface.

In view of the foregoing, it will be understood by those skilled in the art that the methods of the present invention can facilitate operation of laser devices, and in particular medical laser devices exhibiting a capability of producing laser pulses having a plurality of pulse durations. The above-described embodiments have been provided by way of example, and the present invention is not limited to these examples. Multiple variations and modification to the disclosed embodiments will occur, to the extent not mutually exclusive, to those skilled in the art upon consideration of the foregoing description.

For example, a laser-pumping circuit comprising a plurality (e.g., more than two) of high voltage outputs and corresponding pulse-forming networks (e.g., for generating three or more outputs of varying pulse width) is contemplated by the present invention. The present invention may be used with or constructed to implement different laser pulse durations and varying amounts of fluid (e.g., water streams, sprays or mists) in the context of, for example, Erbium-types of lasers, for facilitating, for example, multiple treatment or cutting effects such as hemostatic-type and bleeding-type tissue cutting effects. For example, a wavelength of about 3 μm and pulse durations of 50 μs and 1000 μs may be implemented to provide first and second cutting effects as desired.

The present invention may also be used or constructed with capacitor-charging power supplies in the generation of pulses having variable duration, keeping in mind that such modifications may in some instances present issues such as limited pulse repetition rates, relatively expensive driving circuitry, somewhat rectangular rather than bell-shaped current pulse shapes, and relatively numerous, voluminous and/or heavy capacitors.

While the invention has been described in the context of first and second pulse-forming networks, it is to be understood that greater numbers of pulse-forming networks, each similar to the first and second pulse-forming networks but being constructed for generating pulses of different lengths, are also contemplated. Moreover, while the invention has been described in the context of using a single power supply to generate two pulse outputs for an electromagnetic energy output device, implementations of the present invention using three or more pulse-forming networks may comprise a single power supply or may comprise a number of power supplies that is less than the number of pulse-forming networks.

Additionally, other combinations, omissions, substitutions and modifications will be apparent to the skilled artisan in view of the disclosure herein. Accordingly, the present invention is not intended to be limited by the disclosed embodiments, but is to be defined by reference to the appended claims.

What is claimed is:

1. A method of generating dual pulse outputs for an electromagnetic energy output device, the method comprising:
providing a first high voltage output from a power supply, the first high voltage output being capable of driving, with a first potential, a first pulse-forming network that is configured to generate a first pulse output having a first duration;
providing a second high voltage output from the power supply, the second high voltage output being capable of driving, with a second potential smaller than the first potential, a pulse-forming network that is configured differently to generate responsive to an input a second pulse output having one or more of a greater duration and lower-power relative to a pulse output generated by the first-pulse forming network;
providing a laser-pumping source capable of being pumped by at least one of the first pulse output from the first pulse-forming network and the second pulse output from the second pulse-forming network, whereby (a) the first high voltage output is greater than the second high voltage output, (b) the first pulse-forming network comprises a capacitance that is less than a corresponding capacitance of the second pulse forming network, (c) the first pulse-forming network comprises an inductance that is greater than a corresponding inductance of the second pulse-forming network, (d) a laser pulse having a first duration results by pumping the laser-pumping source with the first pulse output, (e) a laser pulse having a second duration results by pumping the laser-pumping source with the second pulse output; and
outputting laser pulses of the first and second different durations and fluid to a tissue to obtain, respectively, first and second different cutting effects;
whereby the amount of fluid is varied with the first and second durations to obtain the different first and second cutting effects.

2. The method as set forth in claim 1, further comprising generating a plurality of laser pulses by repetitively pumping the laser-pumping source with the first pulse output.

3. The method as set forth in claim 1, further comprising generating a plurality of laser pulses by repetitively pumping the laser-pumping source with the second pulse output.

4. The method as set forth in claim 1, further comprising generating a plurality of laser pulses, each laser pulse having one of a first duration generated by pumping the laser-pumping source with the first pulse output and a second, greater duration generated by pumping the laser-pumping source with the second pulse output.

5. The method as set forth in claim 4, further comprising:
receiving a control input from a user; and
controlling the generating of laser pulses according to the control input.

6. The method as set forth in claim 1, wherein:
the generating of a pulse having a first duration comprises generating a pulse having a duration of about 50 microseconds; and
the generating of a pulse having a second duration comprises generating a pulse having duration of about 1000 microseconds.

7. The method as set forth in claim 1, wherein:
the providing of a first high voltage output comprises providing a voltage of about 1500 volts; and
the providing of a second high voltage output comprises providing a voltage of about 500 volts.

* * * * *